US008823488B2

(12) United States Patent
Wellhoefer et al.

(10) Patent No.: US 8,823,488 B2
(45) Date of Patent: Sep. 2, 2014

(54) MEDICAL TREATMENT SYSTEM AND METHOD FOR OPERATION THEREOF

(75) Inventors: Armin Wellhoefer, Schwaig (DE); Christof Donitzky, Eckental/Eschenau (DE)

(73) Assignee: Wavelight AG, Erlangen (DE)

( * ) Notice: Subject to any disclaimer, the term of this patent is extended or adjusted under 35 U.S.C. 154(b) by 474 days.

(21) Appl. No.: 12/708,811

(22) Filed: Feb. 19, 2010

(65) Prior Publication Data

US 2011/0205019 A1 Aug. 25, 2011

(51) Int. Cl.
*A61B 3/14* (2006.01)
*G06F 7/04* (2006.01)
*G06F 21/62* (2013.01)
*G06F 21/32* (2013.01)
*G06F 19/00* (2011.01)

(52) U.S. Cl.
CPC ........ *G06F 19/3406* (2013.01); *G06F 21/6245* (2013.01); *G06F 21/32* (2013.01)
USPC .......................................... 340/5.82; 600/477

(58) Field of Classification Search
USPC ....................................................... 340/5.82
See application file for complete search history.

(56) References Cited

U.S. PATENT DOCUMENTS

| 7,123,751 | B1 * | 10/2006 | Fujieda .......................... 382/115 |
| 2003/0081742 | A1 * | 5/2003 | Czyszczewski et al. ... 379/93.03 |
| 2004/0183683 | A1 * | 9/2004 | Funahashi .................. 340/573.1 |
| 2005/0228238 | A1 * | 10/2005 | Monitzer ...................... 600/300 |
| 2006/0033619 | A1 * | 2/2006 | Sloan .......................... 340/568.1 |
| 2006/0093190 | A1 * | 5/2006 | Cheng et al. .................. 382/115 |
| 2006/0192921 | A1 * | 8/2006 | Loesel et al. .................. 351/219 |
| 2010/0204571 | A1 * | 8/2010 | DellaVecchia et al. ....... 600/427 |

FOREIGN PATENT DOCUMENTS

WO 2005103999 A2 11/2005

* cited by examiner

*Primary Examiner* — Brian Zimmerman
*Assistant Examiner* — Cal Eustaquio
(74) *Attorney, Agent, or Firm* — Haynes and Boone, LLP

(57) ABSTRACT

A medical device comprises a device adapted to perform a medical procedure; a biometric information sensing device adapted to sense biometric information of a user; a controller adapted to retrieve stored biometric registration information of a user from a storage device in communication with the controller, to determine an identity of the user by comparing the stored biometric registration information and the sensed biometric information, and to prevent performance of the medical procedure if the sensed biometric information does not correspond to the stored biometric registration information.

10 Claims, 6 Drawing Sheets

MEDICAL TREATMENT SYSTEM AND METHOD FOR OPERATION THEREOF

TECHNICAL FIELD

The present invention relates to the field of medical devices for treatment or diagnosis of a medical condition and verifying an identity of a user of the medical device, especially a medical device adapted for performing an optical procedure.

BACKGROUND

In the medical devices known from the prior art, a medical device for performing or diagnosing a medical condition obtains user identity information via a user input device, wherein a user inputs information regarding the identity of the user, such as a name, into the medical device, and the medical device performs certain functions according to the input identity information of the user.

However, the devices of the prior art suffer from the disadvantage that there is a possibility that a user may make a mistake in inputting user identity information, and, thereby, an incorrect identification result may be made. If an incorrect identification is made, a time needed to perform an operation may increase. Further, if the user is a patient, and incorrect information corresponding to the identity of the user is input into the medical device, an incorrect identification result may result in a treatment corresponding to a different patient to be output by the medical device, resulting in a risk of an improper procedure being performed on a patient.

Further, the process of inputting identification information into the medical device by the user requires time.

WO2005/103999 discloses a system for associating patient parameter ancillary information with patient identity data via an assigned radio frequency identification (RFID) card. However, this reference fails to adequately ensure the prevention of incorrect identification, because the RFID tag may be misplaced or even exchanged with an RFID card of another user. Further, this system requires the use of a piece of hardware (the RFID tag) and further requires time from the operator to set up the RFID tag to be associated with the user, resulting in increased labour, expense, and complication of the system.

SUMMARY

In view of the above-mentioned problems of the prior art, a medical device according to claim 1 and a method according to claim 13 is provided. It is an object to provide a medical device and a method for efficiently and securely identifying a user of the medical device, while avoiding the possibility of an incorrect identification result due to incorrect identification information being input by a user.

According to a first aspect of the present invention, a medical device comprises a device adapted to perform a medical procedure; a biometric information sensing device adapted to sense biometric information of a user; a controller adapted to retrieve stored biometric registration information of a user from a storage device in communication with the controller, to determine an identity of the user by comparing the stored biometric registration information and the sensed biometric information, and to prevent performance of the medical treatment if the sensed biometric information does not correspond to the stored biometric registration information.

According to another aspect of the present invention, the biometric information sensing device is one of a retinal information sensing device; an iris information sensing device; a two-dimensional facial shape recognition device; a three-dimensional facial shape information sensing device; a skin texture information sensing device; a fingerprint sensing device; a voice recognition device; a behavioural recognition device; a scleral information sensing device; a pupil information sensing device; and a corneal limbus information sensing device.

According to another aspect of the present invention, the medical procedure is one of a diagnostic procedure and a medical treatment.

According to another aspect of the present invention, the diagnostic information is correlated with the biometric registration information in the storage device, and the controller is adapted to receive the stored diagnostic information correlated with the biometric registration information in the storage device.

According to another aspect of the present invention, the controller is adapted to allow the user to at least one of modify and perform the medical procedure, if the sensed biometric information of the user corresponds to stored biometric registration information corresponding to a user having permission to modify or perform the medical procedure.

According to another aspect of the present invention, a medical treatment system comprises the medical device; and a biometric registration information sensing device adapted to obtain biometric registration information from the user; wherein the storage device, which is in communication with the biometric registration information sensing device, is adapted to the store the biometric registration information obtained by the biometric information sensing device.

According to another aspect of the present invention, the controller is adapted to correlate the input user identity information with the biometric registration information of the user; and the storage device is adapted to store the biometric registration information correlated with user identity information.

According to another aspect of the present invention, the medical treatment system comprises a diagnostic device adapted to obtain diagnostic information from the user.

According to another aspect of the present invention, the diagnostic device comprises the biometric registration information sensing device, and the biometric registration information sensing device is further adapted to obtain the biometric registration information from the user when the diagnostic device obtains the diagnostic information from the user.

According to another aspect of the present invention, a method of comparing biometric information for performing a medical procedure comprises obtaining biometric registration information from a user; storing the biometric registration information correlated with an identity of the user; sensing biometric information from the user; determining whether the sensed biometric information from the user corresponds to the stored biometric registration information; and preventing performance of the medical treatment if the sensed biometric information from the user does not correspond to the stored biometric registration information.

According to another aspect of the present invention, the method of comparing biometric information for performing a medical procedure further comprises identifying one of a plurality of stored biometric registration informations for a plurality of users as corresponding to the sensed biometric information; and obtaining information associated with the identified one of a plurality of stored biometric registration informations.

According to another aspect of the method of the present invention, the obtained information associated with the identified one of a plurality of stored biometric registration informations is identity information of the user.

According to another aspect of the present invention, the medical procedure is a treatment procedure, and the method further comprises receiving diagnostic information and treatment information associated with the biometric registration information corresponding to the sensed biometric information.

According to another aspect of the present invention, the method further comprises obtaining diagnostic information from the user, and storing the diagnostic information in association with the sensed biometric information, wherein the biometric information is obtained when the diagnostic information is obtained.

According to another aspect of the method of the present invention, the steps of sensing biometric registration information and biometric information from the user comprises sensing at least one of retinal information, iris information; corneal information; two-dimensional facial shape information; three-dimensional facial shape information; skin texture information; fingerprint information; voice information; behavioural information; scleral information; pupil information; and corneal limbus information.

According to another aspect of the present invention, if the user is a medical professional, the method further comprises allowing, if the sensed biometric information of the user corresponds to stored biometric registration information, the user to access to at least one of modifying information corresponding to the medical procedure, and performing the medical procedure.

DESCRIPTION OF THE DRAWINGS

The foregoing objects, features, aspects and advantages will become more apparent from the following detailed description when taken in conjunction with the accompanying drawings.

DETAILED DESCRIPTION

Figure 1:
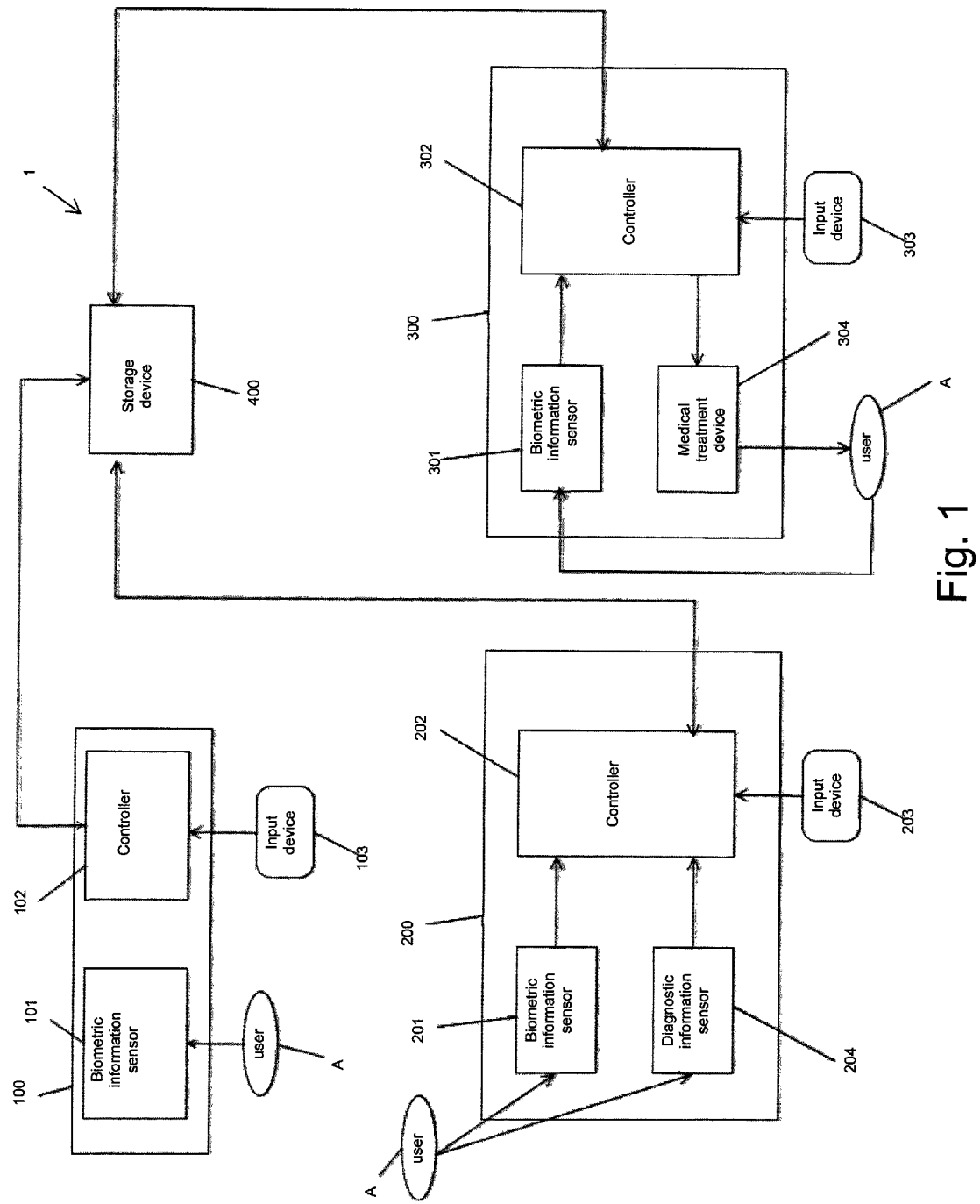
FIG. 1 shows a medical treatment system of the present invention.

Hereinafter, examples of the medical device, medical treatment system, and method of use thereof will be described with reference to the accompanying figures. The same reference numerals are used to refer to identical elements.

According to a first example of the present invention, the medical treatment system 1 comprises a registration device 100, a diagnostic device 200, a treatment device 300, and a storage device 400. The registration device 100, diagnostic device 200, and treatment device 300 are all in communication with the storage device 400 such that information obtained by the registration device 100, diagnostic device 200, and treatment device 300 may be stored in the storage device 400, and information from the storage device 400 may be obtained by each of the registration device 100, diagnostic device 200, and treatment device 300.

Each of the registration device 100, diagnostic device 200, and treatment device 300 comprise a controller 102, 202, 302. The storage device 400 may also comprise a controller 401 (not illustrated). Further, each of the registration device 100, diagnostic device 200, and treatment device 300 may also comprise a display device (not illustrated). Each of the registration device 100, diagnostic device 200, and treatment device 300 may be a standard computer.

Each of the registration device 100, diagnostic device 200, and treatment device 300 comprise a biometric information sensor 101, 201, 301. The biometric information sensor 101, 201, 301 is adapted to detect biometric information from a user A. For example, the biometric information sensor 101, 201, 301 may be one or more of a retinal information sensing device, an iris information sensing device, a two-dimensional facial shape recognition device, a three-dimensional facial shape information sensing device, a skin texture information sensing device, a fingerprint sensing device, a voice recognition device, a behavioural recognition device, a scleral information sensing device, a pupil information sensing device, and a corneal limbus information sensing device. Further examples of biometric information which may be detected for the purposes of identification are also encompassed by the present application. Further, the biometric information sensor 101 is a biometric registration information sensor adapted to receive biometric registration information from the user A.

Still further, each of the registration device 100, diagnostic device 200, and treatment device 300 may comprise an input device 103, 203, 303, adapted to receive inputs and to transmit the inputs to the controller 102, 202, 302 of the respective device. The input device 103, 203, 303 may be a mouse, a keyboard, or another type of input device known in the art.

The registration device receives information corresponding to an identity of a user A, input by the user A or by another operator, into the controller 102 via the input device 103. The registration device may be a computer. Further, the registration device 100 comprises the biometric information sensor 101, adapted to sense biometric registration information of the user A.

The diagnostic device 200, in addition to the biometric information sensor 201, the controller 202, and the input device 203, further comprises a diagnostic information sensor 204 for obtaining diagnostic information from the user A. For example, if the medical treatment system 1 is adapted to perform an optical medical treatment procedure such as an eye surgery, the diagnostic device 200 may comprise a diagnostic information sensor 204 that is adapted to obtain information about the eyes of the user A by, for example, by scanning the retina, cornea, or other parts of the eyes of the user A.

The treatment device 300, in addition to the biometric information sensor 301, the controller 302, and the input device 303, further comprises a medical treatment device 304 for performing a medical treatment on the user A. For example, if the medical treatment system 1 is adapted to perform an optical medical treatment procedure such as an eye surgery, the treatment device 300 may comprise a medical treatment device 304 that is adapted to treat the eyes of the user A by, for example, by performing a laser treatment operation.

A method of operating the medical treatment system according to the first example is described below.

First, a user A is positioned at the registration device 100 such that the biometric information sensor 101 can sense biometric registration information of the user A. An operator, such as a medical professional or medical staff, operates the registration device 100 such that the biometric registration information is obtained from the user A.

If the user A is a patient, the operator may also input information into the controller 102 via the input device 103, for example, information corresponding to the identity of the user A such as a name, address, and other information such as health insurance and billing information. Further, the operator may also input medical information of the user A such as allergies, medical history, etc.

If the user A is a medical professional, the operator may also input information into the controller 102 via the input device 103, for example, information corresponding to the identity of the user A such as a name, qualifications, training, experience, and other information indicative of the medical professional's medical abilities. Further, the operator may input a predetermined decision regarding the permissions granted to the user A for performing medical procedures and/or modifying medical procedures.

Then, the controller 102 transmits the information input by the operator and obtained from the user A to the storage means 400 for storage. The information input by the operator is stored in the storage device 400 with a correlation to the biometric registration information obtained from the biometric information sensor 101.

After the user A is registered, the user A may be transferred to a diagnostic device 200 for performing a diagnosing procedure.

The user A is situated at the diagnostic device such that biometric information may be sensed from the user A via the biometric information sensor 201. Then, biometric information obtained from the user A is analyzed by the controller 202 and is compared to biometric registration information stored in the storage device 400. Then, the controller 202 determines whether the biometric information obtained from the user A matches biometric registration information stored in the storage device 400.

If the biometric information obtained from the user A at the diagnostic device 200 matches biometric registration information stored in the storage device 400, the controller 202 determines the identity of the user A according to the identity information stored as corresponding to the matching biometric registration information in the storage device 400.

If the biometric information obtained from the user A at the diagnostic device 200 does not match any of the biometric registration informations stored in the storage device 400, the diagnostic device 200 may require that the user A return to the registration station 100 to be registered before administering or undergoing the diagnostic procedure.

If the user A is a medical professional and the biometric information sensed by the biometric information sensor 201 corresponds to biometric registration information stored in the storage device 400, the diagnostic device 200 may allow the user A to perform the diagnostic procedure using the diagnostic device 200. Further, the diagnostic device 200 may allow the user A to modify or change the diagnostic procedure performed by the diagnostic device 200. Further, the medical professional may be assigned a privilege level, i.e., the identity of the user A may be associated with an ability to change or modify the diagnostic procedure according to the user's training, medical qualifications, or experience.

Alternatively, if the user A is a patient, the biometric information sensor 201 may be disposed on the diagnostic device 200 such that the biometric information may be obtained simultaneously with the diagnostic procedure. For example, if the diagnostic device 200 is adapted to scan the eyes of a patient, the biometric sensor may obtain biometric information related to the retina, iris, corneal limbus, pupils, scleral information, face shape, or skin texture, etc., of the patient at the same time that the diagnostic information sensor is obtaining information related to the eyes of the patient. Further, it is also possible that the biometric information sensor 201 and the diagnostic information sensor 204 could be combined, such that the diagnostic information sensor 204 is adapted to obtain information that can be used for diagnostic purposes and can also obtain biometric information that can be used to identify a user A. In still another alternative, the information obtained for diagnosis may also be biometric information used to identify the user A.

If the user A is a patient and the biometric information sensed by the biometric information sensor 201 corresponds to biometric registration information stored in the storage device 400, the user A is positioned such that the diagnostic information sensor 204 can obtain diagnostic information from the user A, and the diagnostic information is stored in the storage device 400. Further, the diagnostic information may be stored in the storage device 400 as corresponding to the identity information of the user A, or corresponding to the biometric registration information of the user A.

Further, the diagnostic device 200 may require the identity of the user A that is determined by matching biometric registration information to be verified, for example, via the input device 203.

After completion of the diagnostic procedure, the user A is transferred to the treatment device 300.

If the biometric information obtained from the user A at the treatment device 300 matches biometric registration information stored in the storage device 400, the controller 302 determines the identity of the user A according to the identity information stored as corresponding to the matching biometric registration information in the storage device 400. Further, other information associated with the identity of the user A, such as medical information and diagnostic information, may be retrieved and displayed to the operator.

If the biometric information obtained form the user A at the treatment device 300 does not match any of the biometric registration informations stored in the storage device 400, the treatment device 300 may require that the user A return to the registration station 100 to be registered before administering or undergoing the diagnostic procedure. Further, the medical procedure will be prevented from being administered.

As described with respect to the diagnostic device 200, if the user A is a medical professional and the biometric information sensed by the biometric information sensor 301 corresponds to biometric registration information stored in the storage device 400, the treatment device 300 may allow the user A to perform the treatment procedure using the treatment device 300. Further, the treatment device 300 may allow the user A to modify or change the treatment procedure performed by the treatment device 300. Further, the medical professional may be assigned a privilege level, i.e., the identity of the user A may be associated with an ability to change or modify the treatment procedure according to the user's training, medical qualifications, or experience.

Further, if the user A is a patient and the biometric information sensed by the biometric information sensor 301 corresponds to biometric registration information stored in the storage device 400, the user A is positioned such that the medical treatment device 304 can perform a medical treatment on the user A. Further, diagnostic information associated with the identity of the user A may be retrieved and displayed to the operator.

Then, the operator controls the treatment device 300 to perform a medical treatment on the user A.

Because the biometric sensors 101, 201, 301 are provided to recognize biometric data of the user A, the user can be recognized such that a possibility of error due to a misspelled or incorrect name entered into the input devices 103, 203, 303 resulting in an incorrect identification result of the user A is avoided.

Further, the method of recognition is quick, and reduces time required for inputting user identification information.

If the user A is a medical professional, it is ensured that the medical professional operating the medical treatment system 1 is qualified to operate and/or modify or change the medical treatment of the medical treatment system 1, and further may decrease a danger to a patient of an unqualified person performing or modifying the treatment. Such a feature may have the additional advantage that the malpractice insurance required to perform the medical procedures may be reduced for medical treatment systems 1 having the biometric information identification feature.

Further, if the user A is a patient, the present invention provides the advantage that the possibility of performing a medical treatment previously determined for a different patient, or the possibility of performing a medical treatment based on diagnostic information obtained from a different patient, may be avoided.

Further, if the user is a patient, the advantages are obtained that the patient is quickly and accurately identified, and information regarding the identity, medical history, diagnosis and diagnostic information, and treatment information may be obtained quickly by communicating with a central storage device or central server. Further, the information of the user may be displayed to a medical professional and may be reviewed by the medical professional at each stage of the medical treatment. Therefore, the information of the patient is integrated and is easily and quickly accessible by medical professionals.

Further, because the diagnostic device 200 and the treatment device 300 may require the identity of the user A that is determined by matching biometric registration information to be verified, for example, via the input device 203, it can be ensured that the identity of the user A determined according to the sensed biometric information is correct.

Figure 2:
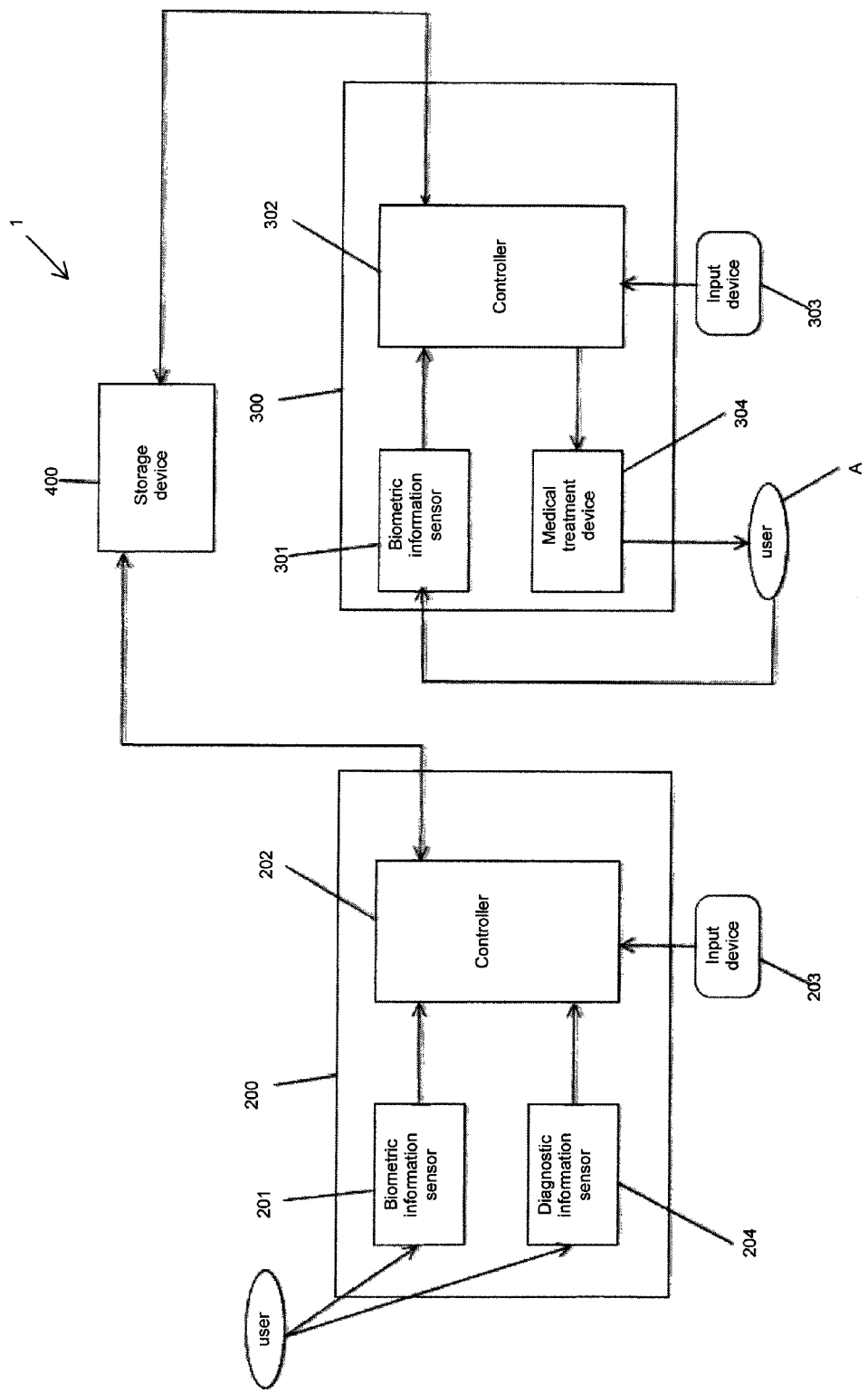
FIG. 2 shows a second example of the medical treatment system of the present invention.

A second example of the present invention is shown in FIG. 2.

The second example is similar to the first example described with respect to FIG. 1, except that the functions of the registration device 100 of the first example are performed by the diagnostic device 200.

Therefore, the user A is not required to first be registered at the registration device 100, but, rather, can be registered at the diagnostic device 200 at the time of diagnosis. Further, the biometric information sensor 201 is adapted to obtain biometric registration information from the user A. This configuration provides the advantages that the number of steps required for the medical treatment is reduced, thereby shortening the overall time of the medical treatment, and reducing time requirements of the operators.

Further, information related to the user A can be input into the diagnostic device 200 at the time that the user is being diagnosed. For example, if the medical treatment requires a scanning operation that lasts a significant amount of time, it may be advantageous to combine the time required to input identification information and medical information of the user A into the medical treatment system 1 with the time required to perform the diagnostic procedure.

Figure 3:
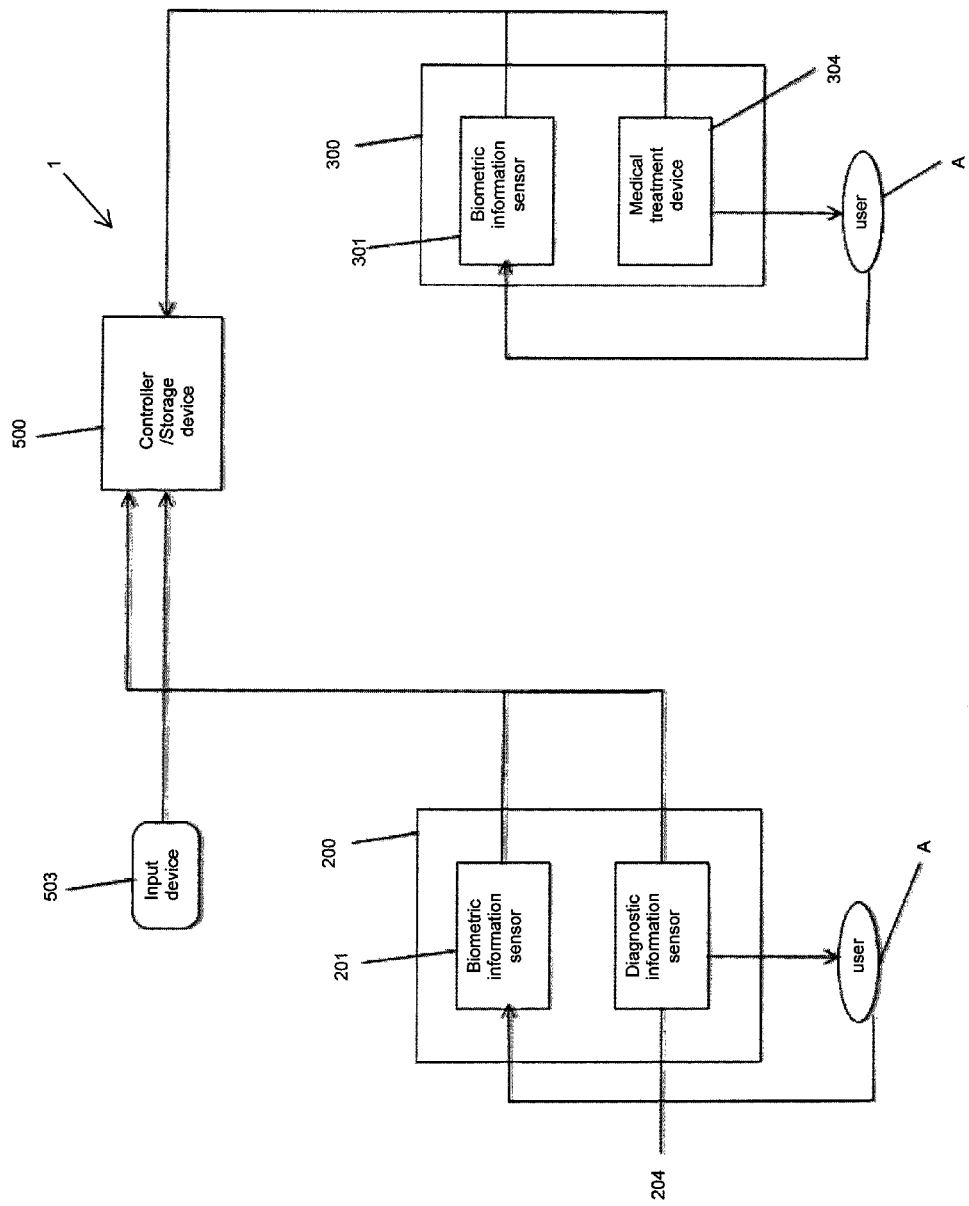
FIG. 3 shows a third example of the medical treatment system according to a third example of the present invention.

The third example, described with respect to FIG. 3, is similar to the second example, described above, except that the diagnostic device 200 and the treatment device 300 are in communication with the storage device 400, wherein the storage device 400 comprises a controller. Further, in the configuration illustrated in FIG. 3, the diagnostic device 200 and the treatment device 300 do not comprise controllers 202, 302.

Such a configuration provides a simplified and economical configuration.

Alternatively, the diagnostic device 200, the treatment device 300, and the storage device 400 could all comprise controllers, such that the communication among the devices is facilitated.

Figure 4:
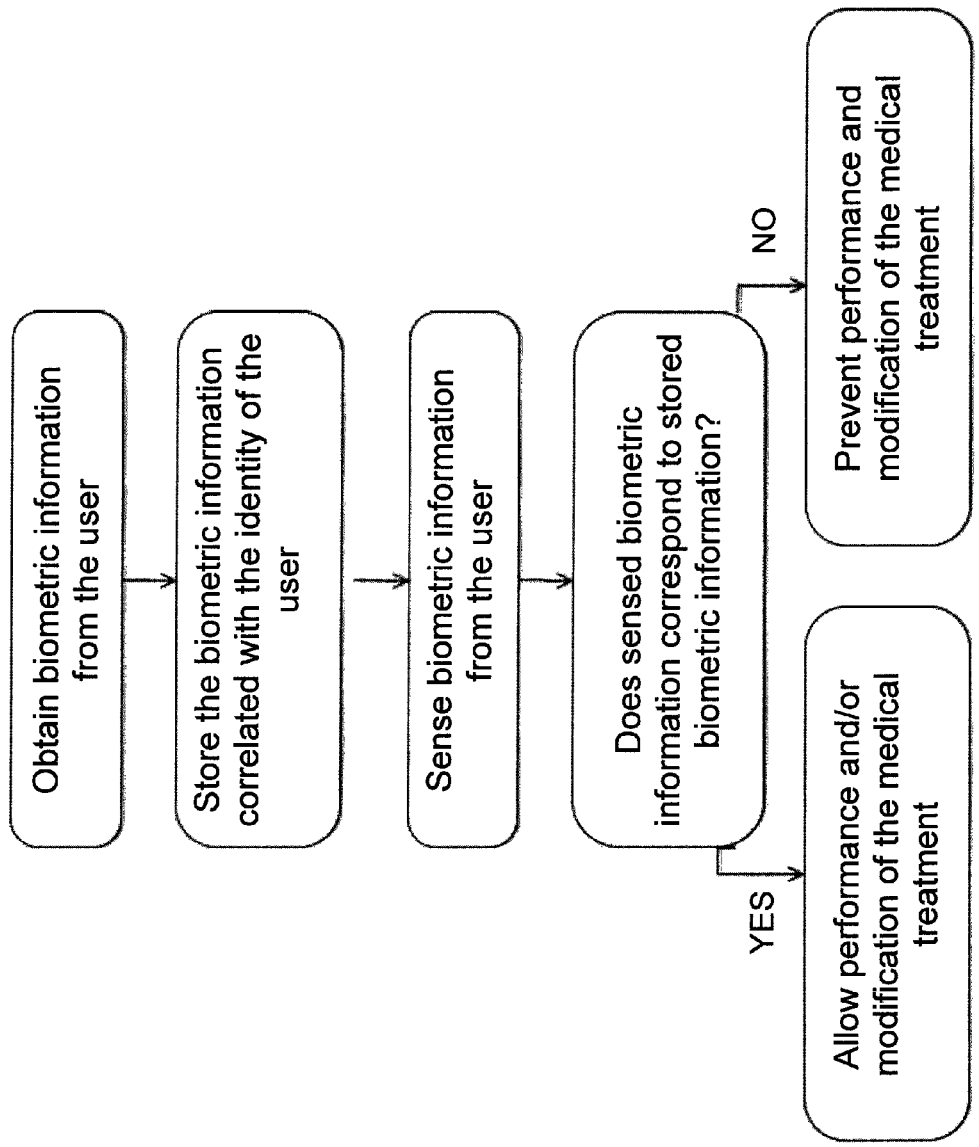
FIG. 4 is an operational flowchart of a method of the present invention.
Figure 5:
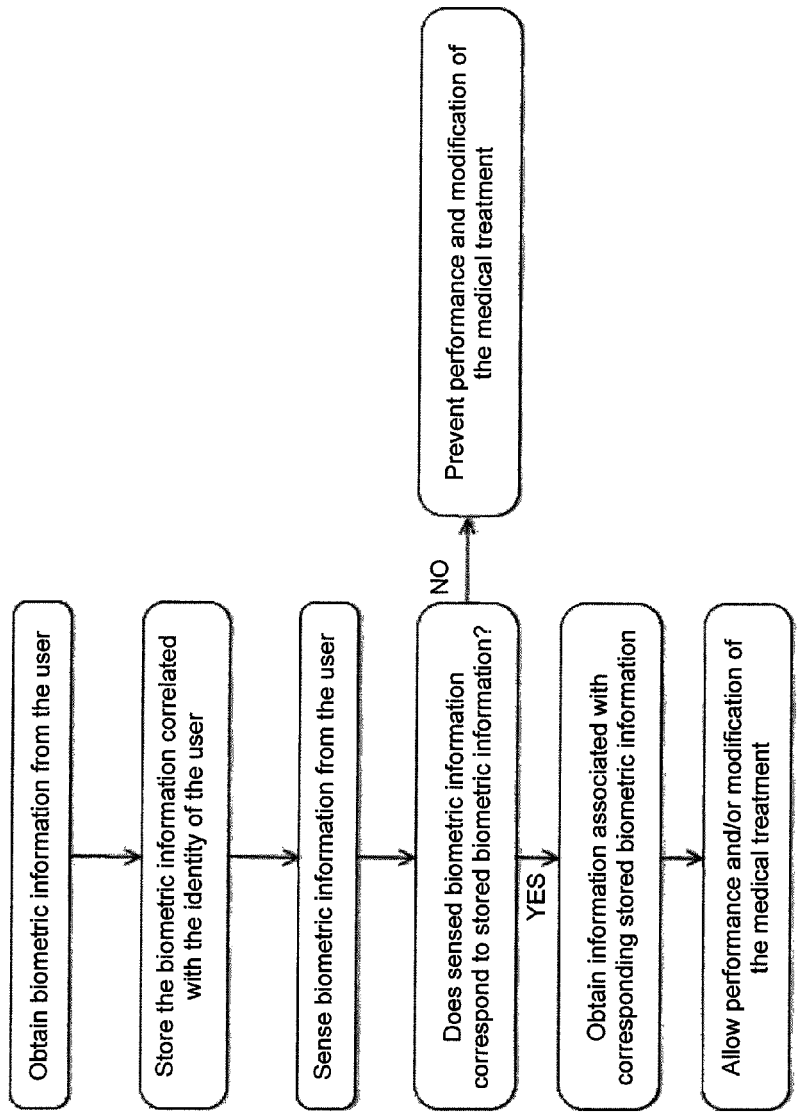
FIG. 5 is an operational flowchart of a second method of the present invention.
Figure 6:
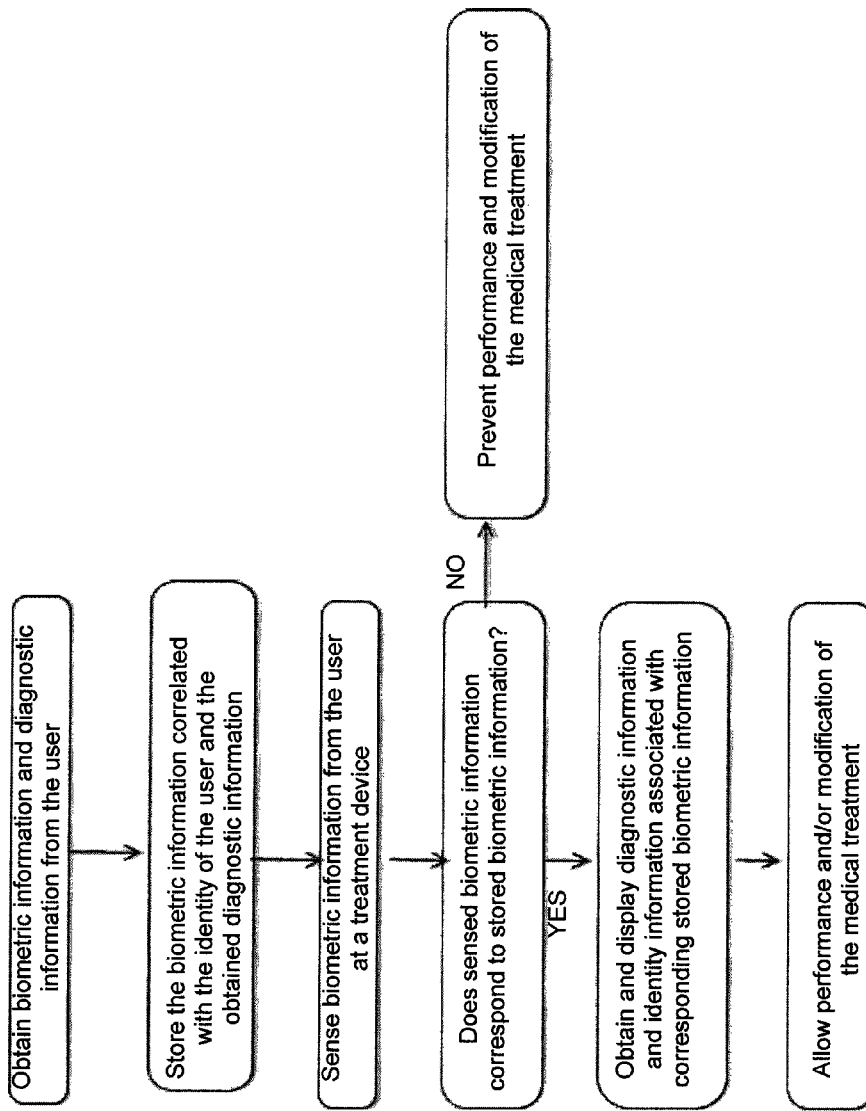
FIG. 6 is an operational flowchart of a third method the present invention.

Exemplary methods of operation of the first, second, and third examples are illustrated in FIGS. 4-6. However, the present invention is not limited to the methods illustrated in FIGS. 4-6.

Although the device and method of the present invention have been described above with respect to a medical treatment system for performing an eye surgery, the features of the present application may be used for a medical treatment system for other types of medical procedures.

Further, although the devices of the medical treatment system have been described with respect to their controllers and storage means, the configuration of the devices is not limited to the configurations shown and illustrated. The devices may each be equipped with a controller and storage means, or each device may communicate with a central controller and storage means, or any of the devices of the medical treatment system may comprise combination of these two configurations.

The biometric information sensors 101, 201, 301 may be similar devices, or may be devices having different characteristics. For example, the registration device 100 may comprise a biometric information sensor 101 adapted to obtain biometric registration information at a higher accuracy, and the biometric information sensors 201, 301 may be of a lower accuracy, and adapted to obtain biometric information at a lower quality sufficient to compare to the biometric registration information obtained by the registration device 100 in order to make a correct judgment regarding the identity of the user A. Such a configuration may provide the advantage that a high quality biometric information sensor need only be disposed in the registration device 100, thus reducing the overall cost of the medical treatment system 1. Alternatively, all biometric information sensors may be similar devices, thus easing the streamlining of the operating and integration of the information obtained by the biometric information sensors.

Having described the preferred examples of the invention referring to the accompanying drawings, it should be understood that the present disclosure is not limited to those precise examples and various changes and modifications thereof could be made by one skilled in the art. Further, although the features of the present invention are described with respect to different examples, it should be understood that the features of any of the examples can be combined with the features of other examples.

The invention claimed is:

1. A method of comparing biometric information for performing a medical procedure, comprising:
   sensing biometric registration information from a user;
   storing the biometric registration information in a database such that the biometric registration information is correlated with an identity of the user;
   sensing biometric information from the user with an information sensing device of a system adapted to perform an optical medical procedure, wherein the information sensing device is adapted to scan at least a portion of an eye of a user to obtain diagnostic information related to the eye of the user and to sense the biometric information from the user;

determining whether the biometric information from the user sensed by the information sensing device of the system adapted to perform the optical medical procedure corresponds to the stored biometric registration information correlated with the identity of the user;

allowing performance of the optical medical procedure if the biometric information from the user sensed by the information sensing device of the system adapted to perform the optical medical procedure corresponds to the stored biometric registration information correlated with the identity of the user, and preventing performance of the medical procedure if the biometric information from the user sensed by the information sensing device of the system adapted to perform the optical medical procedure does not correspond to the stored biometric registration information correlated with the identity of the user;

wherein the step of sensing biometric registration information from the user is performed using a biometric information sensing device of a registration device, the biometric information sensing device being separate and distinct from the information sensing device of the system adapted to perform an optical medical procedure;

wherein the biometric information sensing device of the registration device is configured to sense a biometric parameter associated with the biometric registration information at a first accuracy level and the information sensing device of the system adapted to perform an optical medical procedure is configured to sense the biometric parameter associated with the biometric registration information at a second accuracy level different than the first accuracy level.

2. The method of claim 1, wherein determining whether the biometric information from the user sensed by the information sensing device of the system adapted to perform the optical medical procedure corresponds to the stored biometric registration information correlated with the identity of the user comprises:

identifying one of a plurality of stored biometric registration information for a plurality of users as corresponding to the biometric information sensed by the information sensing device of the system adapted to perform the optical medical procedure; and obtaining information associated with the identified one of a plurality of stored biometric registration information.

3. The method of claim 2, wherein the obtained information associated with the identified one of a plurality of stored biometric registration information is identity information of the user.

4. The method of claim 1, wherein the medical procedure is a treatment procedure, the method further comprising:

receiving diagnostic information and treatment information associated with the stored biometric registration information corresponding to the sensed biometric information.

5. The method of claim 1, further comprising:

obtaining diagnostic information from the user with the information sensing device of a system adapted to perform the optical medical procedure, and storing the diagnostic information in association with the sensed biometric information.

6. The method of claim 1, wherein the steps of sensing biometric information and biometric registration information from the user comprises sensing at least one of retinal information, iris information; two-dimensional facial shape information; three-dimensional facial shape information; skin texture information; scleral information; pupil information; and corneal limbus information.

7. The method of claim 5, wherein the steps of obtaining diagnostic information from the user with an information sensing device and sensing biometric information from the user with an information sensing device are performed simultaneously.

8. The method of claim 1, wherein the information sensing device scans at least a portion of the eye of the user to sense the biometric information from the user.

9. The method of claim 8, wherein the information sensing device scans at least one of a retina and a cornea of the eye.

10. A method of comparing biometric information for performing a medical procedure, comprising:

sensing biometric registration information from a user;

storing the biometric registration information in a database such that the biometric registration information is correlated with an identity of the user;

sensing biometric information from the user with an information sensing device of a system adapted to perform an optical medical procedure, wherein the information sensing device is adapted to scan at least a portion of an eye of a user to obtain diagnostic information related to the eye of the user and to sense the biometric information from the user;

determining whether the biometric information from the user sensed by the information sensing device of the system adapted to perform the optical medical procedure corresponds to the stored biometric registration information correlated with the identity of the user;

allowing performance of the optical medical procedure if the biometric information from the user sensed by the information sensing device of the system adapted to perform the optical medical procedure corresponds to the stored biometric registration information correlated with the identity of the user, and preventing performance of the medical procedure if the biometric information from the user sensed by the information sensing device of the system adapted to perform the optical medical procedure does not correspond to the stored biometric registration information correlated with the identity of the user;

wherein the step of sensing biometric registration information from the user is performed using a biometric information sensing device of a registration device, the biometric information sensing device being separate and distinct from the information sensing device of the system adapted to perform an optical medical procedure;

wherein the biometric information sensing device of the registration device is configured to sense a biometric parameter associated with the biometric registration information at a first accuracy level and the information sensing device of the system adapted to perform an optical medical procedure is configured to sense the biometric parameter associated with the biometric registration information at a second accuracy level equal to the first accuracy level.

* * * * *